United States Patent
Moore et al.

(10) Patent No.: US 11,204,347 B2
(45) Date of Patent: Dec. 21, 2021

(54) OXYGEN SENSOR TEST DEVICE AND METHOD OF TESTING OXYGEN SENSOR

(71) Applicant: Ideal Research Laboratories, LLC, Melvindale, MI (US)

(72) Inventors: Ferrel D. Moore, Lincoln Park, MI (US); James R. Moore, Dearborn, MI (US)

( * ) Notice: Subject to any disclaimer, the term of this patent is extended or adjusted under 35 U.S.C. 154(b) by 108 days.

(21) Appl. No.: 16/357,017

(22) Filed: Mar. 18, 2019

(65) Prior Publication Data

US 2020/0300826 A1 Sep. 24, 2020

(51) Int. Cl.
*G01N 33/00* (2006.01)
*B01D 53/22* (2006.01)

(52) U.S. Cl.
CPC ........... *G01N 33/007* (2013.01); *B01D 53/22* (2013.01); *G01N 33/0014* (2013.01); *G01N 33/0047* (2013.01); *G01N 2033/0072* (2013.01)

(58) Field of Classification Search
CPC ............. G01N 33/007; G01N 33/0014; G01N 33/0047
USPC ........................................................ 73/1.06
See application file for complete search history.

(56) References Cited

U.S. PATENT DOCUMENTS

| 7,640,783 | B2 | 1/2010 | Eickhoff |
| 2001/0018844 | A1 | 9/2001 | Parekh |
| 2006/0101925 | A1 | 5/2006 | Peng et al. |
| 2006/0150711 | A1 | 7/2006 | Hong et al. |
| 2008/0106170 | A1 | 5/2008 | Knowles et al. |
| 2011/0247620 | A1* | 10/2011 | Armstrong ........ A61M 16/0677 128/204.23 |
| 2013/0305807 | A1 | 11/2013 | Wang et al. |

OTHER PUBLICATIONS

Honeywell Fixed Gas Detection Calibration Handbook, https://www.rsd.net/assets/item/735.pdf, dated Apr. 2012, pp. 152.

* cited by examiner

*Primary Examiner* — John Fitzgerald
*Assistant Examiner* — Rodney T Frank
(74) *Attorney, Agent, or Firm* — Stinson LLP

(57) ABSTRACT

A test device for testing of an oxygen sensor uses a compressor to draw air from an external environment and deliver compressed air into a gas separation unit. A gas separation membrane is located in a passage of the gas separation unit such that compressed air from the compressor travels through the passage and passes through the gas separation membrane. The gas separation membrane separates at least one of nitrogen and oxygen from the compressed air to produce a calibration gas having a calibrated amount of oxygen that is different from an amount of oxygen in the air. The calibration gas coupling is configured to be fluidly connected to the oxygen sensor such that the calibration gas is deliverable from the calibration gas coupling to the oxygen sensor.

19 Claims, 3 Drawing Sheets

OXYGEN SENSOR TEST DEVICE AND METHOD OF TESTING OXYGEN SENSOR

FIELD

This disclosure generally pertains to a device and method for testing an oxygen sensor.

BACKGROUND

Oxygen sensors are used to measure an amount of oxygen in a gas. For example, oxygen sensors can be used in industrial settings to determine the amount (e.g., concentration) of oxygen in environmental air. An excess or deficiency of oxygen may indicate an unsafe condition. Oxygen sensors are periodically tested to make sure they are accurately sensing the amount of oxygen in a gas. Typically oxygen sensors are tested by delivering a test gas to the oxygen sensor having a known amount of oxygen. For example, a pressurized cylinder containing test gas having a calibrated amount of oxygen can be coupled to the sensor to deliver the test gas to the oxygen sensor. If the oxygen sensor fails to sense that the test gas has the amount of oxygen that is known to be present in the test gas, it may be determined that the oxygen sensor is no longer accurate.

SUMMARY

In one aspect, a test device for testing of an oxygen sensor comprises a compressor having a compressor outlet. The compressor is configured to draw air from an external environment and deliver compressed air through the compressor outlet. A gas separation unit has an air inlet, a calibration gas coupling, a passage connecting the air inlet to the calibration gas coupling and a gas separation membrane located in the passage such that gas travelling through the passage from the air inlet to the calibration gas coupling passes through the gas separation membrane. The air inlet is fluidly connected to the compressor outlet such that the compressed air flows through the air inlet into the gas separation unit. The gas separation membrane is configured to separate at least one of nitrogen and oxygen from the compressed air to produce a calibration gas having a calibrated amount of oxygen that is different from an amount of oxygen in the air. The calibration gas coupling is configured to be fluidly connected to the oxygen sensor such that the calibration gas is deliverable from the calibration gas coupling to the oxygen sensor.

In another aspect, a method for testing an oxygen sensor comprises delivering compressed air drawn from an external environment through a gas separation membrane of a test device to produce a calibration gas having a calibrated amount of oxygen. The calibration gas is delivered from the gas separation membrane to the oxygen sensor.

Other aspects will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
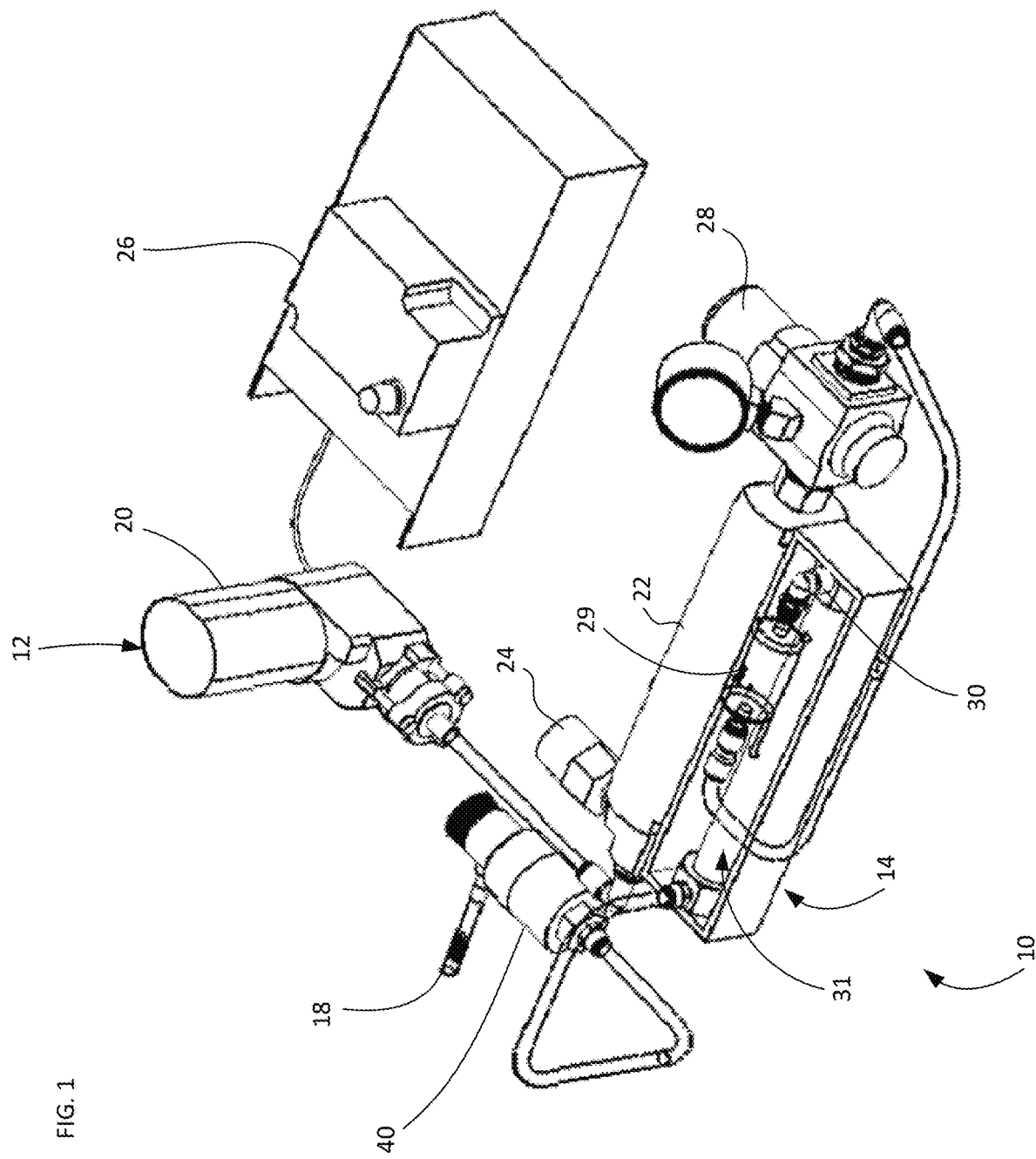
FIG. 1 is a perspective view of a test device.

Referring to FIG. 1, one embodiment of a test device for testing an oxygen sensor is generally indicated at reference number 10. The test device comprises an air compressor, generally indicated at 12, and a gas separation unit, generally indicated at 14. As will be explained below, the air compressor 12 is configured to pump compressed air drawn from an external environment through the gas separation unit 14 to produce a calibration gas having a calibrated amount (e.g., concentration) of oxygen. In certain embodiments, the air compressor 12 and the gas separation unit 14 can be permanently affixed to a common base (not shown). The air compressor 12 and the gas separation unit 14 can also comprise separable components that can be fluidly coupled at the time of use. Generally, the gas separation unit 14 is configured to separate at least one of nitrogen and oxygen from the compressed air to produce the calibration gas. In the illustrated embodiment, the gas separation unit 14 is configured to produce a calibration gas comprising oxygen-deficient air. It is contemplated that other embodiments could be configured to produce a calibration gas comprising oxygen-rich air. The test device 10 has a calibration gas coupling 18 through which the test device is configured to discharge the calibration gas. The coupling 18 is particularly constructed for fluid connection to an oxygen sensor (not shown) such that the calibration gas is deliverable from the calibration gas coupling to the oxygen sensor. For example, in one or more embodiments, the coupling 18 comprises a fitting that is configured to be mechanically fastened to the oxygen sensor to establish a fluid connection between the test device 10 and the oxygen sensor.

In general, the air compressor 12 is configured to draw in air from an external (ambient) environment and deliver compressed air through a compressor outlet to the gas separation unit 14. In one or more embodiments, the air compressor 12 is configured to deliver compressed air through the compressor outlet at a pressure in an inclusive range of from about 40 psi to about 100 psi. As will be explained in further detail below, the pressure of the compressed air is one parameter that can affect the amount of oxygen in the calibration gas produced by the test device 10. It will be appreciated, therefore, that depending on the amount of oxygen that is desired for the calibration gas, other pressures can be used without departing from the scope of the invention.

In the illustrated embodiment, the air compressor 12 comprises a pump 20 (e.g., a displacement pump) that is configured to draw in air from an external environment and pump the air into a compressed air tank 22 (e.g., an accumulator tank). In other embodiments, a tankless air compressor (e.g., a pump that delivers a continuous stream of pressurized air) can be used without departing from the scope of the invention. A pressure sensor 24 is configured to detect a pressure of the compressed air in the tank 22 and send a signal representative of the detected pressure to a pump controller 26. The pump controller is configured to control a motor of the pump to activate the pump as required to maintain a suitable pressure in the compressed air tank 22. For example, in one or more embodiments, the pump controller 26 can be configured to (i) activate the pump 20 when the pressure in the tank 22 falls below a minimum threshold that is greater than the desired pressure for the compressed air delivered to the gas separation unit 14 and (ii) deactivate the pump when the pressure in the tank exceeds a maximum threshold that is greater than the minimum threshold. A pressure regulator 28 is fluidly connected between an outlet of the tank 22 and the compressor outlet and is configured to regulate a pressure at which the compressed air is discharged from the tank through the compressor outlet. In the illustrated embodiment, the test device 10 comprises an air filter 29 that is configured to filter the compressed air before the compressed air is delivered into the gas separation unit 14. In the illustrated embodiment, the pressure regulator 28 is mounted directly on the end of the tank 22, the air filter 29 is connected to the gas separation unit 14 by a rigid fitting, and flexible tubing connects the pump 20 to the tank 22 and connects the pressure regulator 28 to the air filter 29. In other embodiments, other types of fluid connections could be used without departing from the scope of the invention.

Figure 2:
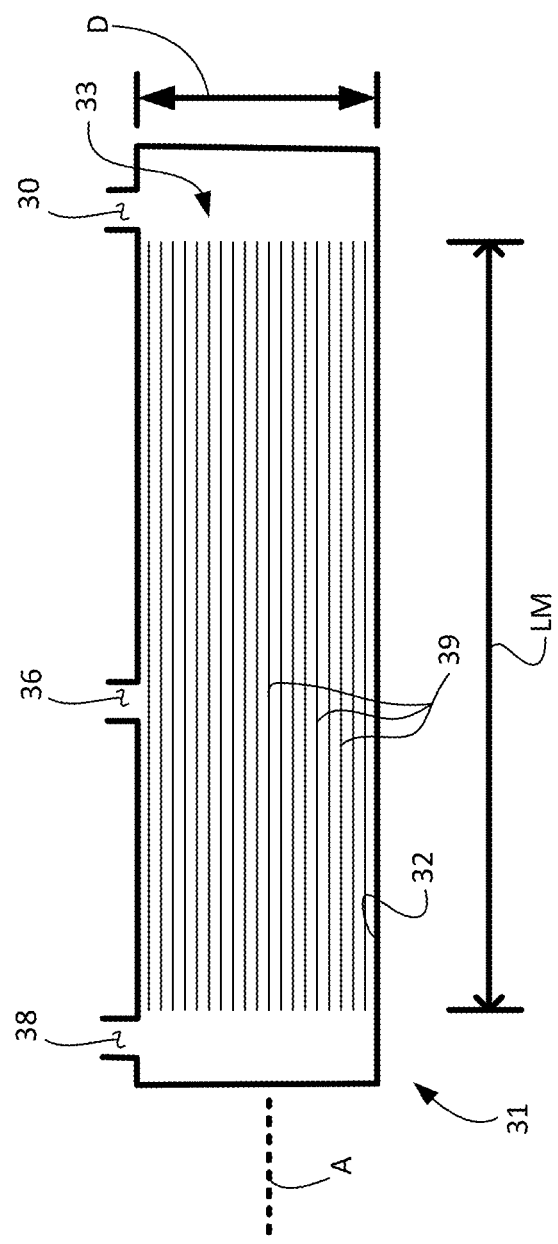
FIG. 2 is a schematic longitudinal cross section of a gas separation unit cartridge of the test device.

The gas separation unit 14 has an air inlet 30 that is fluidly coupled to the outlet of the compressor 12 and includes a passage 32 (FIG. 2) that fluidly connects the air inlet to the calibration gas coupling 18. In the illustrated embodiment, the gas separation unit 14 comprises a cartridge, generally indicated at 31. Referring to FIG. 2, the cartridge 31 defines a portion of the passage 32 through the gas separation unit 14. The cartridge 31 has an axis A along which compressed air flows through the cartridge. A gas separation membrane, generally indicated at 33, is received in the cartridge 31 such that gas flowing through the passage 32 must pass through the gas separation membrane. The air inlet 30 is located adjacent an upstream axial end of the cartridge 31. The gas separation membrane 33 has a length LM that extends along the axis A from an upstream end in fluid communication with the air inlet to a downstream end adjacent a downstream end of the cartridge 31.

In addition to the air inlet 30, the illustrated cartridge 31 also has middle port 36 that extends through a side wall of the cartridge at a location spaced apart between the ends of the gas separation membrane 33 and a downstream port 38 located adjacent a downstream axial end of the cartridge in fluid communication with the downstream end of the gas separation membrane. In the illustrated embodiment, the middle port 36 is fluidly connected to atmosphere such that the middle port functions as an exhaust port. The downstream port 38 in the illustrated embodiment is fluidly coupled to the calibration gas coupling 18 such that the downstream port functions as a calibration gas port of the cartridge 31. As explained in greater detail below, when compressed air is delivered through the gas separation membrane 33, calibration gas comprising oxygen-deficient air is discharged from the downstream end of the gas separation membrane 33 and flows through the calibration gas port 38 and exhaust gas comprising oxygen-rich air permeates radially through the side of the gas separation membrane 33 and flows through the exhaust gas port 36. In other embodiments, the cartridge could have other configurations without departing from the scope of the invention. For example, it is expressly contemplated that the middle port 36 could be fluidly coupled to the calibration gas coupling 18 and the downstream port 38 could be used as an exhaust port such that oxygen-rich air directed through the middle port is used as a calibration gas.

Any suitable gas separation membrane can be used without departing from the scope of the invention. In the illustrated embodiment, the gas separation membrane comprises a nitrogen separation membrane. Suitable nitrogen separation membranes are sold under the name PRISM® membranes by Air Products and Chemicals, Inc. of Trexlertown, Pa. The nitrogen separation membrane 33 comprises a plurality of membrane fibers 39. The illustrated membrane 33 is generally cylindrical and has a diameter D and a length LM extending along the axis A of the cartridge 31. The membrane fibers 39 extend along the length LM (FIG. 2) of the membrane 33. In one or more embodiments the length LM of the membrane 33 is in an inclusive range of from about 12 cm to about 40 cm (e.g., about 18 cm). The diameter D of the membrane 33 can be in an inclusive range of from about 1 cm to about 3 cm (e.g., about 2 cm) in certain embodiments. Membrane dimensions are a parameter that affects how much nitrogen the membrane 33 separates from the air as it pumped through the gas separation unit 14. Thus, it will be appreciated that membrane dimensions can vary depending upon the desired amount of oxygen for the calibration gas.

The nitrogen separation membrane 33 is configured to separate nitrogen from the compressed air as it flows along the axis A through the cartridge 31. Separated nitrogen flows along the length LM of the membrane 33 such that gas discharged from the downstream end of the membrane is rich in nitrogen and deficient in oxygen. This oxygen-deficient air is directed to flow through the downstream calibration gas port 38 in the illustrated embodiment. The gas from which the nitrogen is separated permeates radially through the membrane 33 such that gas discharged from the side of the membrane is deficient in nitrogen and rich in oxygen. This oxygen-rich air is directed to flow through the middle exhaust gas port 36 in the illustrated embodiment.

Referring again to FIG. 1, the illustrated gas separation unit 14 further comprises a flow regulator 40 that is configured to regulate a flow rate at which the calibration gas is delivered through the calibration gas coupling 18 to the oxygen sensor. The flow regulator 40 is fluidly coupled between the calibration gas port 38 and the calibration gas coupling 18 such that the flow regulator regulates the flow rate at which the calibration gas flows from the cartridge 31 through the calibration gas coupling 18. In one or more embodiments, the flow regulator 40 comprises a restricted orifice that limits the flow rate at which the calibration gas can flow through the restricted orifice at the pressure provided by the air compressor 12. In certain embodiments, the calibration gas flow rate is in an inclusive range of from about 0.25 LPM to about 6.0 LPM and more preferably from about 0.25 LPM to about 1.0 LPM. In one or more embodiments, the regulator comprises an adjustable regulator configured to selectively adjust the calibration gas flow rate. The pressure regulator 28 and the flow regulator 40 control back pressure in the cartridge 31 as the air compressor delivers compressed air through the cartridge. Back pressure in the cartridge is one parameter that affects the amount of oxygen in the calibration gas. In certain embodiments, the test device 10 is configured such that the back pressure in the cartridge 31 is about the same as the inlet pressure (e.g., in an inclusive range of from about 40 psi to about 100 psi). However, it will be appreciated that other back pressures can be used to achieve the desired amount of oxygen in the calibration gas.

In an exemplary method of using the test device 10, a user fluidly connects the calibration gas coupling 18 to an oxygen sensor and activates the air compressor 12. The air compressor 12 draws air from the environment into the air compressor and fills the tank 22 with compressed air. The pressure regulator 28 discharges compressed air at a desired pressure and the air filter 29 filters the compressed air before it flows through the air inlet 30 into the gas separation unit 14. The compressed air flows along the axis A of the cartridge 31 through the nitrogen separation membrane 33. The fibers 39 (FIG. 2) separate nitrogen from the compressed air such that oxygen-deficient calibration gas is discharged radially from the downstream axial end of the membrane 33 and oxygen-rich exhaust gas is discharged from the side of the membrane. The oxygen-deficient calibration gas flows through the calibration gas port 36 and the oxygen-rich exhaust gas flows through the exhaust gas port 38. The regulator 40 regulates the rate at which the calibration gas flows through the calibration gas coupling 18 to the oxygen sensor and maintains a desired back pressure in the cartridge 31.

It has been found that when an oxygen separation membrane 33 of a given length LM and diameter D is used and the back pressure and flow rate of compressed air flowing through the cartridge 31 is maintained at about predefined levels (e.g., under expected ambient temperature and altitude conditions), the test device 10 can reliably and consistently produce a calibration gas having a known amount (e.g., concentration) of oxygen. The calibration gas produced by the illustrated test device 10 thus has a calibrated amount oxygen. During testing, the output reading from the oxygen sensor is compared with the calibrated amount of oxygen. If the output reading deviates from the calibrated amount of oxygen, the user can take corrective action to recalibrate or repair the oxygen sensor. If the output reading is about the same as the calibrated amount of oxygen, the user can determine that the oxygen sensor is functioning properly. In some embodiments, an oxygen concentration of the oxygen-deficient air is in an inclusive range of from about 0.2% to about 20%, and in other embodiments from about 10% to 20%.

In certain embodiments, the user can adjust one or more parameters of the test device 10 to adjust the amount of oxygen in the calibration gas produced by the test device. For example, the user can adjust the calibrated amount of oxygen by adjusting a back pressure in the gas separation membrane 33, for example, by adjusting an outlet pressure of the pressure regulator 28 or regulated flow rate of the flow regulator 40. Still other parameters can be adjusted to adjust the calibrated amount of oxygen in the calibration gas.

Figure 3:
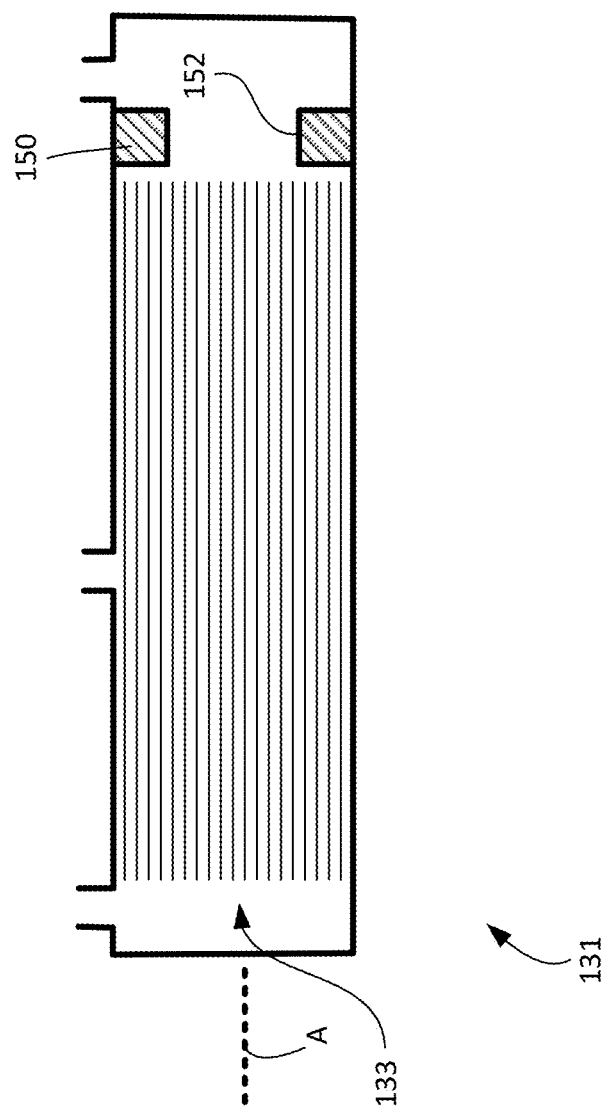
FIG. 3 is a schematic longitudinal cross section of another embodiment of a gas separation unit cartridge.

Referring to FIG. 3, another embodiment of a gas separation cartridge is generally indicated at reference number 131. The gas separation cartridge 131 is similar in many respects to the gas separation cartridge 31, and corresponding parts are given corresponding reference numbers, plus 100. Like the cartridge 31, the cartridge 131 is configured to direct compressed air to flow along an axis A through a gas separation membrane 133. Unlike the cartridge 31, the cartridge 131 is configured to restrict the compressed air from flowing along a cross-sectional portion of the membrane 133. In the illustrated embodiment, the gas separation cartridge 131 comprises an orifice plate 150 defining an orifice 152. The orifice plate 150 is disposed so that effectively all gas that flows through the cartridge 131 must pass through the orifice 152. The cartridge 131 has a cross-sectional flow area, and the orifice 152 has a cross-sectional flow area that is less than the cross-sectional flow area of the cartridge. That is, the orifice plate 150 defines a restricted orifice 152 and blocks flow into the membrane 133 through a portion of the cross-sectional flow area of the cartridge 131. The illustrated orifice plate 150 is located adjacent the upstream end of the cartridge 131. The portion of the cross-sectional area of the gas separation membrane into which compressed air is permitted to flow is another parameter that can affect the amount of nitrogen separation that occurs in the gas separation membrane In one or more embodiments, the cartridge 131 is configured such that the size and/or shape of the restricted orifice 152 is adjustable. For example, the orifice plate 150 can comprise an adjustment mechanism (not shown) that is configured to selectively adjust the cross-sectional flow area of the orifice 152. In certain embodiments, a gas separation unit can comprise a plurality of interchangeable orifice plates 150 having orifices 152 of different sizes. For example, a gas separation unit can comprise an orifice plate receiver (not shown) that is configured to selectively receive any of the interchangeable orifice plates and position each received orifice plate such that effectively all of the compressed air must pass through the orifice therein. Since the size of cross-sectional area of the membrane 133 into which compressed air is permitted to flow is one factor that affects the amount of nitrogen separation that occurs during use, it can be seen that facilitating changes in the cross-sectional size of the restricted orifice 152 allows for adjustments to be made in the calibrated amount of oxygen that is present in the calibration gas.

As explained above, in certain embodiments of methods of testing an oxygen sensor, a user of a test device can adjust parameters of the test device that change the calibrated amount of oxygen in the calibration gas produced by the test device. In addition to the parameters discussed above, in one or more embodiments, the user can adjust the cross-sectional flow size of the orifice 152 of the orifice plate 150 (e.g., by replacing the orifice plate with an interchangeable orifice plate or using an adjustment mechanism of the orifice plate). Adjusting the cross-sectional flow size of the restricted orifice 152 is one method of adjusting the size of a cross-sectional portion of the membrane 133 into which compressed air is configured to flow, but other ways of adjusting the size of this cross-sectional portion of the membrane can be used in other embodiments.

As can be seen, the test device 10 can be used to test an oxygen sensor without using a pressurized canister or any other gas source besides environmental air. The test device 10 can be used at low pressures and without any valves. The amount of oxygen in the calibration gas that is delivered to the oxygen sensor can be predictably controlled by adjusting one or more adjustable parameters of the test device. Thus, the test device 10 can consistently deliver to an oxygen sensor a calibration gas that has a calibrated amount of oxygen that is appropriate for testing the oxygen sensor.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A test device for testing of an oxygen sensor, comprising:
    a compressor having a compressor outlet, the compressor being configured to draw air from an external environment and deliver compressed air through the compressor outlet; and
    a gas separation unit having an air inlet, a calibration gas coupling, a passage connecting the air inlet to the calibration gas coupling and a gas separation membrane located in the passage such that gas travelling through the passage from the air inlet to the calibration gas coupling passes through the gas separation membrane, the air inlet being fluidly connected to the compressor outlet such that the compressed air flows through the air inlet into the gas separation unit, the gas separation membrane being configured to separate at least one of nitrogen and oxygen from the compressed air to produce a calibration gas having a calibrated amount of oxygen that is nonzero and different from an amount of oxygen in the air, the calibration gas coupling forming an outlet of the test device through which the calibration gas is discharged out of the test device and the calibration gas coupling being configured to selectively fluidly connect the test device to the oxygen sensor such that the calibration gas is discharged from the calibration gas coupling to the oxygen sensor;

wherein the compressor is configured to deliver compressed air to the air inlet at a pressure in an inclusive range of from 40 psi to 100 psi.

2. A test device as set forth in claim 1, wherein the gas separation unit comprises a cartridge that defines at least a portion of the passage connecting the air inlet to the calibration gas coupling.

3. A test device as set forth in claim 2, wherein the gas separation membrane is received in the cartridge.

4. A test device as set forth in claim 3, wherein the gas separation membrane has an oxygen-deficient gas outlet and an oxygen rich gas outlet.

5. A test device as set forth in claim 4, wherein the calibration gas coupling is in fluid communication with the oxygen-deficient gas outlet.

6. A test device as set forth in claim 4, wherein the gas separation unit comprises an exhaust passage that fluidly couples the oxygen rich gas outlet to the external environment.

7. A test device as set forth in claim 1, wherein the gas separation unit comprises a flow regulation orifice fluidly coupled between the cartridge and the calibration gas coupling.

8. A test device as set forth in claim 7, wherein the flow regulation orifice is configured to regulate calibration gas flowing through the flow regulation orifice to a flow rate in an inclusive range of from 0.25 LPM to 6.0 LPM.

9. A test device as set forth in claim 2, wherein the cartridge has a length in an inclusive range of from 15 cm to 40 cm.

10. A test device as set forth in claim 1, wherein the compressor comprises a compressed air tank.

11. A test device as set forth in claim 10, wherein the compressor comprises a pressure regulator fluidly connected between the compressed air tank and the air inlet.

12. A test device as set forth in claim 10, wherein the compressor comprises a pump configured to pump the air from the external environment into the compressed air tank.

13. A test device as set forth in claim 12, wherein the compressor further comprises a pump controller that is configured to selectively activate the pump to maintain a pressure of the compressed air in the compressed air tank.

14. A test device according to claim 1, further comprising an air filter configured to filter the compressed air before the compressed air is delivered through the air inlet of the gas separation unit.

15. A test device as set forth in claim 1, wherein the calibration gas coupling is configured to releasably connect to the oxygen sensor.

16. A test device as set forth in claim 1, wherein the calibration gas is oxygen-deficient air.

17. A test device for testing of an oxygen sensor, comprising:
a compressor having a compressor outlet, the compressor being configured to draw air from an external environment and deliver compressed air through the compressor outlet; and
a gas separation unit having an air inlet, a calibration gas coupling, a passage connecting the air inlet to the calibration gas coupling and a gas separation membrane located in the passage such that gas travelling through the passage from the air inlet to the calibration gas coupling passes through the gas separation membrane, the air inlet being fluidly connected to the compressor outlet such that the compressed air flows through the air inlet into the gas separation unit, the gas separation membrane being configured to separate at least one of nitrogen and oxygen from the compressed air to produce a calibration gas having a calibrated amount of oxygen that is nonzero and different from an amount of oxygen in the air, the calibration gas coupling forming an outlet of the test device through which the calibration gas is discharged out of the test device and the calibration gas coupling being configured to selectively fluidly connect the test device to the oxygen sensor such that the calibration gas is discharged from the calibration gas coupling to the oxygen sensor;
wherein the gas separation unit comprises a flow regulation orifice fluidly coupled between the cartridge and the calibration gas coupling; and
wherein the flow regulation orifice is configured to regulate calibration gas flowing through the flow regulation orifice to a flow rate in an inclusive range of from 0.25 LPM to 6.0 LPM.

18. A test device for testing of an oxygen sensor, comprising:
a compressor having a compressor outlet, the compressor being configured to draw air from an external environment and deliver compressed air through the compressor outlet; and
a gas separation unit having an air inlet, a calibration gas coupling, a passage connecting the air inlet to the calibration gas coupling and a gas separation membrane located in the passage such that gas travelling through the passage from the air inlet to the calibration gas coupling passes through the gas separation membrane, the air inlet being fluidly connected to the compressor outlet such that the compressed air flows through the air inlet into the gas separation unit, the gas separation membrane being configured to separate at least one of nitrogen and oxygen from the compressed air to produce a calibration gas having a calibrated amount of oxygen that is nonzero and different from an amount of oxygen in the air, the calibration gas coupling forming an outlet of the test device through which the calibration gas is discharged out of the test device and the calibration gas coupling being configured to selectively fluidly connect the test device to the oxygen sensor such that the calibration gas is discharged from the calibration gas coupling to the oxygen sensor;
wherein the compressor comprises a compressed air tank;
wherein the compressor comprises a pressure regulator fluidly connected between the compressed air tank and the air inlet; and wherein the pressure regulator is configured to regulate compressed air delivered through the air inlet to a pressure in a range of from 40 psi to 100 psi.

19. A test device for testing of an oxygen sensor, comprising:
- a compressor having a compressor outlet, the compressor being configured to draw air from an external environment and deliver compressed air through the compressor outlet; and
- a gas separation unit having an air inlet, a calibration gas coupling, a passage connecting the air inlet to the calibration gas coupling and a gas separation membrane located in the passage such that gas travelling through the passage from the air inlet to the calibration gas coupling passes through the gas separation membrane, the air inlet being fluidly connected to the compressor outlet such that the compressed air flows through the air inlet into the gas separation unit, the gas separation membrane being configured to separate at least one of nitrogen and oxygen from the compressed air to produce a calibration gas having a calibrated amount of oxygen that is nonzero and different from an amount of oxygen in the air, the calibration gas coupling being configured to be fluidly connected to the oxygen sensor such that the calibration gas is deliverable from the calibration gas coupling to the oxygen sensor;

wherein the calibration gas is oxygen-deficient air wherein an oxygen concentration of the oxygen-deficient air is in an inclusive range of from 0.2% to 20%.

* * * * *